United States Patent

Ohno et al.

[11] Patent Number: 5,171,763
[45] Date of Patent: Dec. 15, 1992

[54] CURABLE COMPOSITION

[75] Inventors: Hideki Ohno, Moriya; Takesi Satou; Hidenori Okamoto, both of Tsukuba, all of

[73] Assignee: Tokuyama Soda Kabushiki Kaisha, Yamaguchi, Japan

[21] Appl. No.: 804,377

[22] Filed: Dec. 10, 1991

[30] Foreign Application Priority Data

Dec. 14, 1990 [JP] Japan ................................. 410542
Mar. 29, 1991 [JP] Japan ................................. 89437

[51] Int. Cl.$^5$ ............... A61K 6/083; C08F 22/10; C08K 3/34; C08K 3/20
[52] U.S. Cl. ....................... 523/116; 524/432; 524/436; 524/443; 526/318
[58] Field of Search ............ 523/116; 524/432, 436, 524/443, 559; 526/318

[56] References Cited

U.S. PATENT DOCUMENTS

| | | | |
|---|---|---|---|
| 4,148,988 | 4/1979 | Masuhara et al. | 526/318 |
| 4,775,592 | 10/1988 | Akahane et al. | 523/116 |
| 4,918,136 | 4/1990 | Kawaguchi et al. | 526/318 |

FOREIGN PATENT DOCUMENTS

WO88/05652  8/1988  PCT Int'l Appl.
2000789  1/1979  United Kingdom .

Primary Examiner—Paul R. Michl
Assistant Examiner—Peter Szekely
Attorney, Agent, or Firm—Wenderoth, Lind & Ponack

[57] ABSTRACT

There is provided a curable composition for dental restoration comprising a vinyl monomer containing not less than 30% by weight of an acid group-containing vinyl monomer represented by the formula

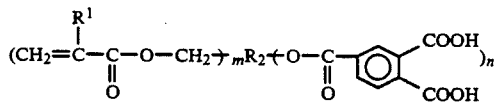

wherein $R^1$'s may be the same or different and each denotes a hydrogen atom or a methyl group, $R^2$ denotes a trivalent to hexavalent organic residue having 1 to 30 carbon atoms which residue may have an ether linkage and/or an ester linkage, m is an integer of 2 to 4, n is an integer of 1 or 2, an ion dissolving filler that dissolves a polyvalent metallic ion, and a polymerization initiator. Said curable composition features that it shows high adhesion even under humidity, and its cured product has high strength and less coloration.

3 Claims, No Drawings

CURABLE COMPOSITION

DETAILED DESCRIPTION OF THE INVENTION

1. Industrial Utilization Field

This invention relates to a novel curable composition. More specifically, this invention relates to a curable composition which provides a cured product having high tensile strength, which has a hydrophilic surface of a biological hard tissue such as a tooth substance, a metallic material, a ceramic material, etc. even under humidity, and which shows high adhesive strength to a metallic element-containing product.

2. Prior Art

In recent years, a composite resin, a glass ionomer cement, amalgam, etc. have been used to restore relatively small defective portions of teeth given by caries, etc. Above all, the composite resin and the glass ionomer cement have been often used as aesthetic materials because of their appearance close to that of teeth.

Nevertheless, various clinical problems have been pointed out on these two dental filling materials.

For example, the composite resin is, though showing high mechanical strength, devoid itself of adhesion to a tooth, and a bonding agent has to be therefore used in filling. Disadvantageously, the use of such a bonding agent not only makes clinical operation intricate but also heavily decreases adhesion strength when water enters an oral cavity during its use. Another problem is that even if using the bonding agent, adhesive strength between the composite resin and a tooth, especially, its dentin is insufficient. Accordingly, in a boundary portion with a gingiva called a cervical area, a dentin appears on the surface of the tooth, so that drop of the composite resin often becomes at issue.

Meanwhile, the glass ionomer cement is a material which is more hydrophilic than the composite resin and adheres to the tooth without using the bonding agent. Said cement therefore dispenses with such a complicated bonding procedure as is done in the composite resin; however, it is low in mechanical strength as a material itself therefore cannot apply to a site on which stress is exerted.

Various types of adhesive monomers have been developed to improve adhesion between the composite resin and the tooth. For instance, Japanese Laid-open Patent Application (Kokai) No. 38749/1982 discloses 2-(3,4-dicarboxybenzoyloxy)-1,3-dimethacryloyloxy-propane. The curable composition using this monomer, however, makes it easy to adhere a color component to the surface of the cured product and is poor in mechanical strength. Japanese Laid-open Patent Application (Kokai) No. 127717/1986 discloses a curable composition comprising a poly(meth)acrylate of a bisphenol polyepoxy compound, a (meth)acryloyloxyl group-containing aromatic polycarboxylic acid or its acid anhydride, a (meth)acrylic acid ester compound, an inorganic filler and a curing agent.

However, this composition is cured by radical polymerization of an olefin component. When said composition is used as a filler material, it is disadvantageously poor in adhesive strength to a tooth and is easy to discolor upon absorbing colored ingredients of food and beverage in the oral cavity.

PROBLEMS THE INVENTION SEEKS TO SOLVE

As has been stated above, a filling material has been demanded that eliminates the need of the intricate operations, surely adheres to the tooth even under humidity, and has less coloration and sufficient strength.

MEANS FOR SOLVING THE PROBLEMS

The present inventors have made assiduous investigations to conquer the aforesaid technical problems, and consequently have found that a composition comprising an acid group-containing vinyl monomer of a specific structure, a specific ion leachable filler and a polymerization initiator, even if cured under humidity, surely adheres to a tooth, and shows less coloration and sufficient strength as its cured product. This finding has led to completion of this invention.

Namely, this invention provides a curable composition for dental restoration comprising (A) 100 parts by weight of a vinyl monomer containing not less than 30% by weight of an acid group-containing vinyl monomer represented by formula [I]

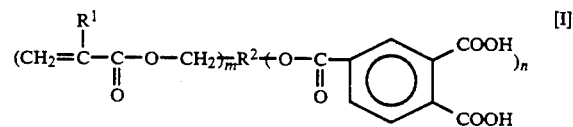

wherein $R^1$'s may be the same or different and each denotes a hydrogen atom or a methyl group, $R^2$ denotes a trivalent to hexavalent organic residue having 1 to 30 carbon atoms which residue may have an ether linkage and/or an ester linkage, m is an integer of 2 to 4, and n is an integer of 1 or 2, (B) 30 to 500 parts by weight of an ion leachable filler that dissolves 2 mgeq/g to 60 mgeq/g of a polyvalent metallic ion, and (C) 0.1 to 3 parts by weight of a polymerization initiator.

In formula [I] $R^2$ is a trivalent to hexavalent hydrocarbon residue having 1 to 30 carbon atoms which residue may have an ether linkage and/or an ester linkage.

Examples of the hydrocarbon group are:

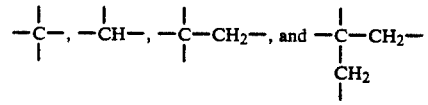

Examples of the hydrocarbon group having the ether linkage in the main chain are:

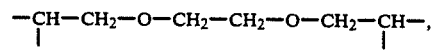

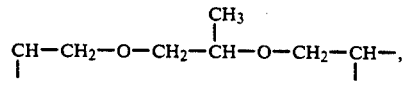

and

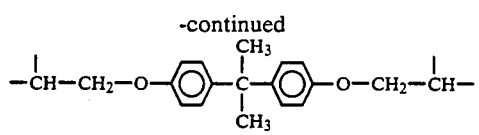
Preferable examples of the acid group-containing vinyl monomer of formula [I] having the ester linkage in the main chain are:
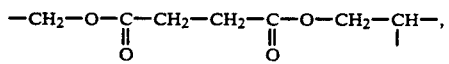
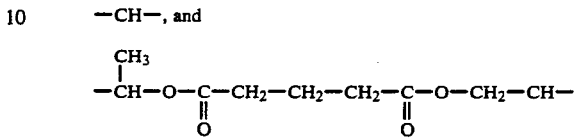
Preferable examples of the acid group-containing vinyl monomer of formula [I] are:
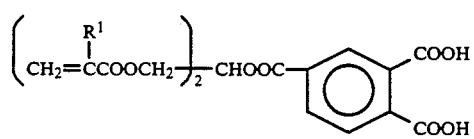
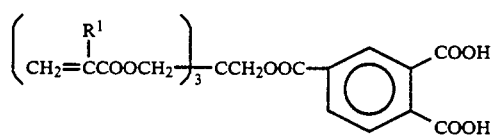
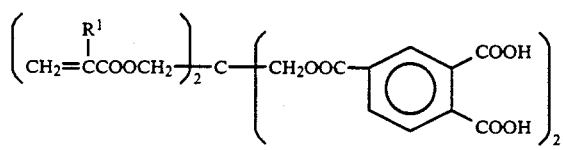
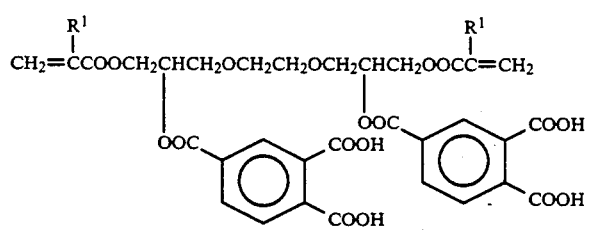
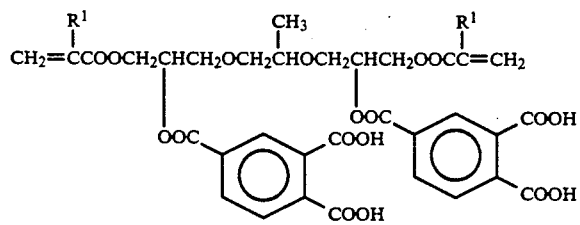
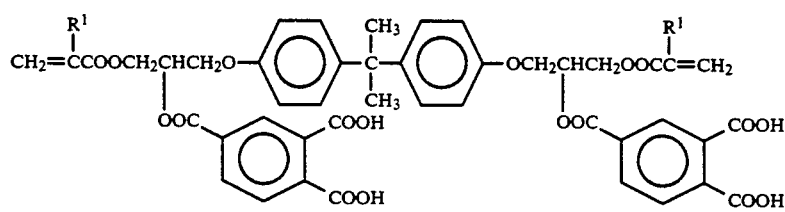

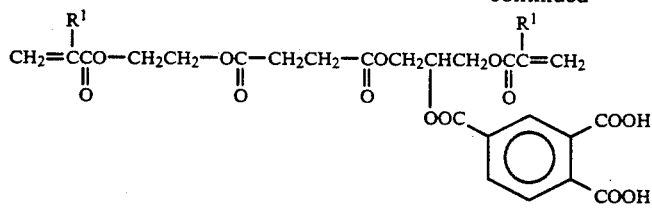

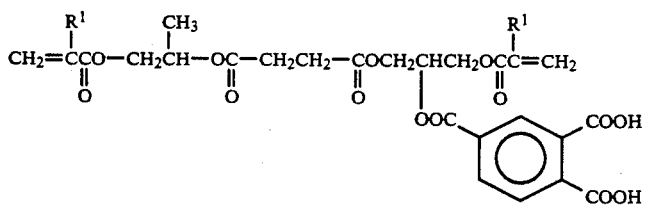

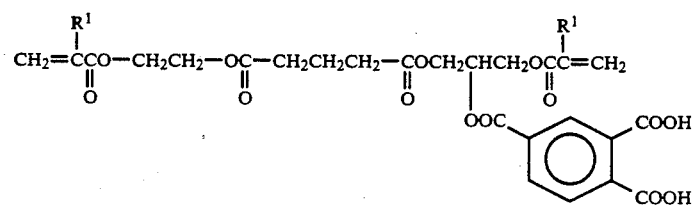

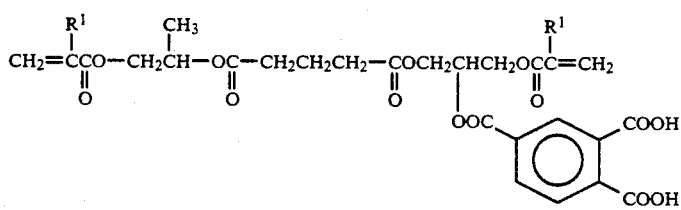

wherein $R^1$ is as defined above.

A method for producing the acid group-containing vinyl monomer of formula [1] is not particularly limited, and any method is available. An industrially preferable method is as follows.

The acid group-containing vinyl monomer of formula [1] is formed by reacting a vinyl compound represented by formula [2]

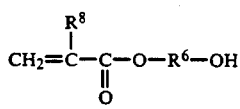  [2]

wherein $R^8$ denotes a hydrogen atom or a methyl group, and $R^6$ denotes an alkylene group having 1 to 4 carbon atoms,
with a dicarboxylic acid represented by formula [3]

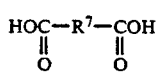  [3]

wherein $R^7$ denotes an alkylene group having 1 to 4 carbon atoms,
or its anhydride to obtain a monocarboxylic acid vinyl monomer, then reacting it with an epoxy compound represented by formula [4]

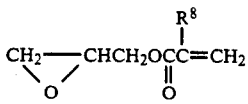  [4]

wherein $R^8$ denotes a hydrogen atom or a methyl group, to obtain a monohydroxylvinyl monomer, and adding a trimellitic acid compound.

As the vinyl compound of formula [2], any known compounds can be used. Preferable examples thereof are 2-hydroxyethyl methacrylate, 2-hydroxyethyl acrylate, 2-hydroxypropyl methacrylate, 2-hydroxypropyl acrylate, 2-hydroxybutyl methacrylate, and 2-hydroxybutyl acrylate.

As the dicarboxylic acid of formula [3], any known compounds can be used. Preferable examples thereof are succinic acid, glutaric acid, adipinic acid and their anhydrides.

As the epoxy compound of formula [4], glycidyl methacrylate is preferable, and as the trimellitic acid compound used in the above reaction, anhydrotrimellitic acid chloride is preferable.

In the above reaction, the reaction molar ratio of the dicarboxylic acid of formula [3] to the vinyl compound of formula [2] is preferably 1 to 2, more preferably 1.0 to 1.5. The reaction catalyst used at this time can be any known catalyst. Examples thereof are aliphatic amines such as triethylamine and trimethylamine, and pyridine. The amount of the catalyst is preferably 0.1 to 1 mol per mol of the compound of formula [1]. Examples of the solvent used in this reaction are tetrahydrofuran, dioxane and dimethylsulfoxide. The reaction temperature is 30° to 80° C., preferably 40° to 70° C. The reaction time is not particularly limited, and can usually be selected within the range of 1 to 50 hours; it may be determined within such a range that the reaction product is not polymerized, relative to the reaction temperature. It is advisable to add a small amount of a polymerization inhibitor. Examples of the polymerization inhibitor are hydroquinone, hydroquinone monomethyl ether, and butylhydroxytoluene. After the reaction, the solvent is removed under reduced pressure, and the residue is dissolved in a water-insoluble solvent such as benzene and washed with an acid such as hydrochloric acid to remove the reaction catalyst. After washing, the product is extracted into an aqueous layer with a weak alkali such as sodium carbonate, and washed with an organic solvent such as ether. Subsequently, the product is re-extracted into the organic layer with an acid such as dilute hydrochloric acid and a water-insoluble solvent such as ethyl acetate, and the solvent is then removed under reduced pressure to obtain a high-purity product.

The reaction molar ratio of the epoxy compound of formula [4] to the monocarboxylic acid vinyl monomer obtained by the reaction of the vinyl compound of formula [2] with the dicarboxylic acid of formula [3] in the above reaction is preferably 1 to 2, more preferably 1.0 to 1.5. As the reaction catalyst used at this time, known compounds are available. Examples thereof are p-toluenesulfonic acid, pyridine, triethylamine, triethylbenzylammonium chloride and trimethylamine. Above all, p-toluenesulfonic acid is preferable. The amount of the reaction catalyst is preferably 0.1 to 1 mol per mol of the monocarboxylic acid vinyl monomer. This reaction may be performed in the absence or presence of a solvent. Benzene, toluene, xylene, chloroform, diethyl ether, tetrahydrofuran, dioxane and dimethyl sulfoxide can be used as the solvent as required. The reaction temperature can be selected within the range of room temperature to 100° C., and is preferably within the range of room temperature to 80° C. The reaction time is not particularly limited, and can be selected within the range of 1 to 30 hours; it may be determined within such a range that the reaction product is not polymerized, relative to the reaction temperature. It is also advisable to add a small amount of a polymerization inhibitor. Examples of the polymerization inhibitor are hydroquinone, hydroquinone monomethyl ether, and butylhydroxytoluene. In case of using the water-insoluble reaction solvent, purification can be conducted by washing the reaction solution with water or a weak alkali such as a sodium carbonate aqueous solution. In case of using the water-soluble reaction solvent, purification can be conducted by replacing the solvent with a water-insoluble solvent such as benzene and then effecting the above washing.

The reaction molar ratio of the trimellitic acid compound such as anhydrotrimellitic acid chloride to the monohydroxyvinyl monomer resulting from the reaction between the monocarboxylic acid vinyl monomer and the epoxy compound of formula [4] is 0.5 to 1.5, preferably 0.9 to 1.2. As the reaction catalyst used at this time, any known compounds are available. Examples thereof are pyridine, triethylamine and trimethylamine. The amount of the reaction catalyst is 1 to 2 mols, preferably 1 to 1.5 mols per mol of the monohydroxyvinyl monomer. Examples of the solvent used in this reaction are benzene, toluene, xylene, chloroform, diethyl ether, tetrahydrofuran, dioxane, and dimethyl sulfoxide. The reaction temperature can be selected within the range of 0° to 100° C. Since the reaction is a remarkable exothermic reaction, the initial reaction temperature of 0° to 50° C. is preferable to avoid polymerization of the reaction product The reaction time is not particularly limited, and can usually be selected within the range of 30 minutes to 3 hours. It is also advisable to add a small amount of a polymerization inhibitor. Examples of the polymerization inhibitor are hydroquinone, hydroquinone monomethyl ether, and butyl hydroxytoluene. After the reaction, when the catalyst such as a hydrochloric acid salt is precipitated as a solid, it can be removed by filtration; even when not precipitated as a solid, it can be removed with water-washing. In case of using trimellitic acid chloride as the trimellitic acid compound, water is added to the reaction solution after removal of the catalyst and the mixture is strongly stirred at about room temperature to hydrolyze the anhydride into a dicarboxylic acid. The rate of hydrolysis can be increased by the co-existence of the water-soluble solvent such as tetrahydrofuran. The temperature of the hydrolysis reaction can be selected within the range of 10° to 40° C., and the reaction time is about 3 to 50 hours. After the hydrolysis reaction, the solution is dehydrated to remove the solvent. There can be obtained the intended acid group-containing vinyl monomer.

In the curable composition of this invention, it is advisable to add, the other vinyl monomer to the acid group-containing vinyl monomer. Typical examples of the other vinyl monomer are those having an acrylic group and/or a methacrylic group. Concrete examples thereof are as follows.

a) Monofunctional monomer:
methyl (meth)acrylate, ethyl (meth)acrylate, hydroxyethyl (meth)acrylate, tetrahydrofurfuryl (meth)acrylate, glycidyl (meth)acrylate, acrylic acid, methacrylic acid, p-methacryloxybenzoic acid, N-2-hydroxy-3-methacryloxypropyl-N-phenylglycine, 4-methacryloxyethyltrimellitic acid, its anhydride, 6-methacryloxyhexamethylenemalonic acid, 10-methacryloxydecamethylenemalonic acid, 2-methacryloxyethyldihydrogene phosphate, 10-methacryloxydecamethylenedihydrogen phosphate, and 2-hydroxyethylhydrogenphenyl phosphate.

b) Difunctional vinyl monomer:
(i) Aromatic compound:
2,2-bis(methacryloxyphpenyl)propane, 2,2-bis[4-(3-methacryloxy)-2-hydroxypropoxyphenyl)-propane, 2,2-bis(4-methacryloxyethoxyphenyl)-propane, 2,2-bis(4-methacryloxydiethoxyphenyl)propane, 2,2-bis(4-methacryloxytetraethoxyphenyl)propane, 2,2-bis(4-methacryloxypentaethoxyphenyl)propane, 2,2-bis(4-methacryloxydipropoxyphenyl)propane, 2(4-methacryloxyethoxyphenyl)2(4-methacryloxydiethoxyphenyl)propane, 2(4-methacryloxydiethoxyphenyl)-2(4-methacryloxytriethoxyphenyl)propane, 2-(4-methacryloxydipropoxyphenyl)-2(4-methacryloxytriethoxyphenyl)propane, 2,2-bis(4-methacryloxydipropoxyphenyl)propane, 2,2-bis(4-methacryloxyisopropoxyphenyl)propane, and their acrylates.
(ii) Aliphatic compound:
ethylene glycol dimethacrylate, diethylene glycol dimethacrylate, triethylene glycol dimethacrylate, butylene glycol dimethacrylate, neopentyl glycol dimethacrylate, propylene glycol dimethacrylate, 1,3-butanediol dimethacrylate, 1,4-butanediol dimethacrylate, 1,6-hexanediol dimethacrylate, and their acrylates.

c) Trifunctional vinyl monomer:
trimethylolpropane trimethacrylate, trimethylolethane trimethacrylate, pentaerythritol trimethacrylate, trimethylolmethane trimethacrylate, their acrylates, and monomers represented by the following formulas.

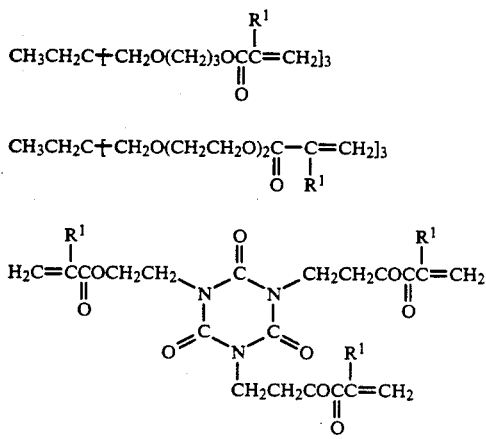

wherein $R^1$ is as defined above.

d) Tetrafunctional vinyl monomer
pentaerythritol tetramethacrylate, pentaerythritol tetraacrylate, and urethane monomers represented by the following formulas.

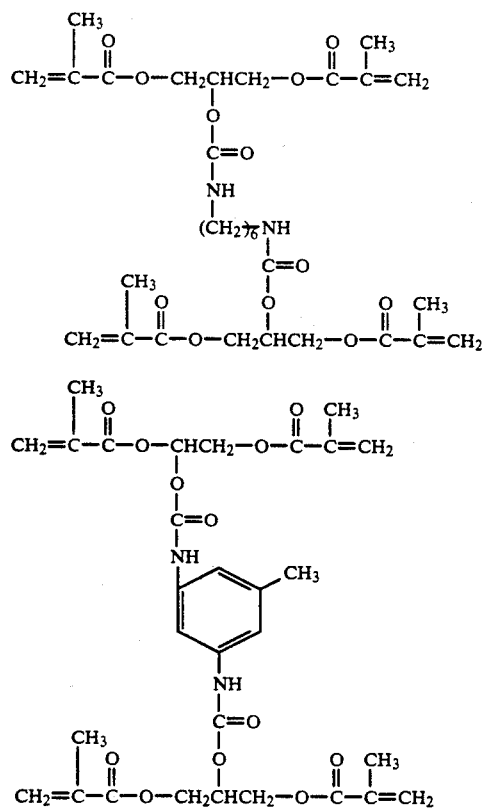

The above other vinyl monomers can be used either singly or in combination.

The amount of the other vinyl monomer relative to the acid group-containing vinyl monomer is preferably 0 to 70% by weight, more preferably 5 to 50% by weight. Unless the other vinyl monomer is added, the viscosity of the monomer becomes high, making poor operability; when the amount is larger than 70% by weight, adhesion between the curable composition and the tooth tends to decrease.

The ion leachable filler used in this invention dissolves 2 mgeq/g to 60 mgeq/g, preferably 5 mgeq/g to 30 mgeq/g of polyvalent metallic ions. When the polyvalent ion dissolving amount of the ion leachable filler is larger than 60 mgeq/g, a major part of the filler dissolves and tensile strength of the cured product decreases. When the polyvalent ion dissolving amount of the ion dissolving filler is smaller than 2 mgeq/g, a color component is liable to adhere to the surface of the cured product. By the way, in this invention, the ion dissolving amount of the filler means an amount of ions dissolving when 1 g of the filler is dippped in 50 ml of an acrylic acid aqueous solution having pH of 2.2 at a temperature of 37° C. The polyvalent metallic ion means a divalent or higher metallic ion capable of bonding with the acid group of the acid group-containing vinyl monomer. Typical examples thereof are ions of metals such as calcium, strontium, varium, aluminum, zinc and lanthanoid.

The ion dissolving filler is not particularly limited if it meets the above conditions. Preferable examples thereof are hydroxides such as calcium hydroxide and strontium hydroxide, and oxides such as zinc oxide and a fluoroaluminosilicate glass. Of these, the fluoroaluminosilicate glass is most preferable in the aspect of color resistance of the cured product.

As the fluoroaluminosilicate glass, a known product used as a dental cement, e.g., a glass ionomer cement, is available. The ordinary fluoroaluminosilicate glass has a composition of, by ion weight, 10–33% of silicon, 4–30% of aluminum, 5–36% of an alkaline earth metal, 0–10% of an alkali metal, 0.2–16% of phosphorus, 2–40% of fluorine, and a remainder of oxygen. Said glass is preferably used. A more preferable composition is, by ion weight, 15–25% of silicon, 7–20% of aluminum, 8–28% of an alkaline earth metal, 0–10% of an alkali metal, 0.5–8% of phosphorus, 4–40% of fluorine and a remainder of oxygen. It is preferable to replace part or the whole of the alkaline earth metal with magnesium, strontium or barium. Above all, strontium is preferably used because it gives the cured product X-ray impermeability and high strength. As the alkali metal, sodium is quite common, but part or the whole thereof may be replaced with lithium or potassium. It is also possible to replace, as required, part of aluminum with titanium, yttrium, zirconium, hafnium, tantarm or lanthanum. It is further possible to replace the above component with other component unless heavily impairing properties of the cured product.

The amount of the ion leachable filler used in this invention is 30 to 500 parts by weight, preferably 50 to 400 parts by weight per 100 parts by weight of the total amount of the vinyl monomer. When the amount of said filler is less than 30 parts by weight, adhesive strength in a boundary between the curable composition and the tooth substance becomes insufficient; when it is larger than 500 parts by weight, it is difficult to uniformly mix the acid group-containing vinyl monomer with the ion dissolving filler.

The shape of the ion leachable filler used in this invention is not particularly limited, and it may be particles obtained by ordinary pulverization or spherical particles which can be mixed with plate-like or fibrous particles as required.

The particle size of the ion leachable filler is not particularly limited. For example, when the filler is filled in a tooth, it is advisable that the surface of the cured product is smooth; the particle size is 50 micrometers or less, preferably 20 micrometers or less. When the particle size is too small, the surface area of the ion leachable filler becomes great, and it is difficult to mix a large amount of the filler with the acid group-containing vinyl monomer, decreasing tensile strength of the cured product. For this reason, the lower limit of the preferable particle size of the ion leachable filler is 0.01 micrometer.

The polymerization initiator used in this invention is not particularly limited, and any known radical generating agent is available. Preferable examples thereof are organic peroxides such as benzoyl peroxide, p-chlorobenzoyl peroxide, 2,4-dichlorobenzoyl peroxide, acetyl peroxide, lauroyl peroxide, tert-butyl peroxide, cumenehydroperoxide, 2,5-dimethylhexane 2,5-dihydroperoxide, methyl ethyl ketone peroxide, and tert-butylperoxybenzoate, azo compounds such as azobisisobutylonitrile, and organic compounds such as tributylboric acid.

It is also possible to perform polymerization at room temperature by using a combination of the organic peroxide with an amine. The amine is preferably a secondary or tertiary amine with an amino group bonded to an aryl group in the aspect of curing acceleration. Preferable Examples of the amine are N,N-dimethyl-p-toluidine, N,N'-dimethylaniline, N'-beta-hydroxyethylaniline, N,N'-di(beta-hydroxyethyl)aniline, N,N'-di(beta-hydroxyethyl)-p-toluidine, and N-methylaniline, and N-methyl-p-toluidine.

It is advisable to use, as a polymerization initiator, a photosensitizer that generates a radical by light irradiation. Examples of the photosensitizer to ultraviolet rays are benzoin, benzoin methyl ether, benzoin ethyl ether, acetone benzophenone, p-chlorobenzophenone, and p-methoxybenzophenone. A photosensitizer that starts polymerization with a visible light is more preferably used because ultraviolet rays harmful to human body are unnecessary. Examples thereof are benzyl, camphorquinone, alpha-naphthyl, acetonaphthene, p,p'-dimethoxybenzyl, p,p'-dichlorobenzylacetyl, pentanedione, 1,2-phenanthrenequinone, 1,4-phenanthrenequinone, 3,4-phenanthrenequinone, 9,10-phenanthrenequinone, and naphthoquinone. Above all, camphorquinone is most preferable. It is also advisable to use a combination of the photosensitizer with a photopolymerization accelerator.

Examples of the photopolymerization accelerator are tertiary amines such as N,N-dimethylaniline, N,N-diethylaniline, N,N-di-n-butylaniline, N,N-dibenzylaniline, N,N-dimethyl-p-toluidine, N,N-diethyl-p-toluidine, N,N-dimethyl-m-toluidine, p-bromo-N,N-dimethylaniline, m-chloro-N,N-dimethylaniline, p-dimethylaminobenzaldehyde, p-dimethylaminoacetophenone, p-dimethylaminobenzoic acid, p-dimethylaminobenzoic acid ethyl ester, p-dimethylaminobenzoic acid aminoester, N,N-diemthylanthranilic acid methyl ester, N,N-dihydroxyethylaniline, N,N-dihydroxyethyl-p-toluidine, p-dimethylaminophenetyl alcohol, p-dimethylaminostilbene, N,N-dimethyl-3,5-xylidine, 4-dimethylaminopyridine, N,N-dimethyl-alpha-naphthylamine, N,N-dimethyl-beta-naphthylamine, tributylamine, tripropylamine, triethylamine, N-methyldiethanolamine, N-ethylidiethanolamine, N,N-dimethylstearylamine, N,N-dimethylaminoethyl methacrylate, N,N-diethylaminoethyl methacrylate, and 2,2'-(n-butylimino)diethanol; and barbituric acids such as 5-butylbarbituric acid, and 1-benzyl-5-phenylbarbituric acid. These photopolymerization accelerators can be used either singly or in combination.

The amount of the polymerization initiator may properly be determined; it is usually 0.1 to 3% by weight based on the total amount of the vinyl monomer.

The packing mode of the curable composition in this invention is not particularly limited. Either a mode of packing the acid group-containing vinyl monomer, the ion leachable filler and the polymerization initiator (in case of the photosensitizer) in one pack, or a mode of packing the acid group-containing vinyl monomer and the ion leachable filler in two packs and adding the polymerization initiator in one of the packs is available; it can be selected according to the use.

EXAMPLES

This invention is illustrated specifically by the following Production Examples, Examples and Comparative Examples, but is not limited thereto.

Methods for measuring properties of materials described in the descriptive part and the following Examples are as follows.

(1) Particle size distribution of a filler:

A filler was dispersed in water and the particle size thereof was measured with a particle size distribution analyser (manufactured by Malvern). The measurement is based on a diffused diffraction image by a laser beam.

(2) Crystal structure of a filler:

A crystal structure (form) of a filler was determined by an X-ray diffraction measuring device (manufactured by Nippon Denshi K. K.)

(3) Polyvalent metallic ion dissolving amount of a filler:

One gram of a filler was added to 50 ml of a 10 wt.% acrylic acid aqueous solution (pH=2.2), and after stirring at 37° C. for 24 hours, the dissolving ion amount was measured by an atomic-absorption photometer (manufactured by Shimadzu Seisakusho).

(4) Compressive strength of a cured product:

A curable composition was cured in a mold having 3 mm×4 mm φ holes, and then maintained at 37° C. for 1 hour. Curing was conducted for 30 seconds by irradiation with Wite Lite (a visible light irradiating device of Takara Bellmont K. K.) as required.

Subsequently, the cured product was withdrawn from the mold, and dipped in water of 37° C. for 71 hours. Compressive strength of the cured product was then measured by Tensilon (manufactured by Toyo Baldwin K. K.) at a crosshead speed of 1 mm/min.

(5) Tensile strength of a cured product:

A curable composition was cured in a mold having 3 mm×6 mm φ holes and then maintained at 37° C. for 1 hour. Curing was conducted for 30 seconds by irradiation with White Light (a visible light irradiating device of Takara Bellmont K. K.) as required.

Subsequently, the cured product was withdrawn from the mold, and dipped in water of 37° C. for 71 hours. Tensile strength was then measured by Tensilon (manufactured by Toyo Baldwin K. K.) at a crosshead speed of 1 mm/min upon exerting a load in a diametrical direction of the cured product.

Tensile strength was calculated by the following equation.

*Tensile strength $(kg/cm^2) = 2P/0.18\pi$*

*P: breaking load $(kg/cm^2)$*

(6) Adhesion strength to dentin:

A bovine tooth was polished with a #800 emery paper by injecting water to give a surface of a dentin. A double-coated tape having 4 mm $\phi$ holes was adhered to the surface, and a 3 mm-thick paraffin wax having 6 mm $\phi$ holes was adhered thereto such that said tape and wax were concentrically adhered. A curable composition was filled in the circular holes, then cured, and dipped in water at 37° C. for 24 hours. Then, a stainless steel rod 8 mm in diameter and 18 mm in length was fixed on the surface of the cured product with an instantaneous adhesive. A tensile load (crosshead speed 10 mm/min) was exerted between the bovine tooth and the stainless steel rod with Tensilon, thereby measuring adhesive strength between the dentin and the cured product. Adhesive strength under humidity was measured by the above method after thinly coating water on the surface of the dentin with a sponge before filling the curing composition.

(7) Color test:

A cured product was produced in the same method of measuring tensile strength. The cured product was dipped in a 7.4% aqueous solution of an instant coffee (trademark: Nescaffe Excela) at 37° C. for 24 hours. Change in color $\Delta E^*$) before and after dipping was measured by a color difference meter (manufactured by Nippon Denshoku K. K.). The smaller the $\Delta E^*$ value, the lesser the change in color, i.e., the lesser the coloration.

Adhesive strengths of the composite resin and the glass ionomer cement were measured in the same way after filling and curing them according to their instructions.

PRODUCTION EXAMPLE 1

A 300 ml eggplant type flask was charged with 55 g of beta-methacryloyloxyethyl hydrosuccinate (HOMS: a trademark for a product of Kyoei Yushi Kagaku Kogyo K. K.), 28 g of glycidyl methacrylate (made by Wako Junyaku K. K.), 11.4 g of p-toluenesulfonic acid, and 100 ml of chloroform, and they were stirred at room temperature for 2 hours. After 200 ml of chloroform was added to the reaction liquid, the mixture was washed with 300 ml of water, 300 ml of a 1N sodium carbonate aqueous solution and 300 ml of water again in this sequence. The organic layer was dried with the addition of 10 g of anhydrous sodium sulfate, and filtered, followed by removing the solvent under reduced pressure. There resulted 73 g of a colorless liquid.

A 500 ml eggplant type flask was charged with 32 g of anhydrotrimellitic acid chloride, 13 g of pyridine and 200 ml of benzene. With stirring under ice cooling, a solution of 57 g of the colorless liquid in 100 ml of benzene was added dropwise over a period of 1 hour, and the reaction solution was returned to room temperature and then stirred for 1 hour. The solution was filtered to remove pyridine hydrochloride, and the solvent was removed from the filtrate under reduced pressure. To the resulting product were added 250 ml of tetrahydrofuran and 250 ml of water, and the mixture was stirred overnight. Three-hundred milliliters of chloroform were added to this solution to extract the product which was then washed twice with 400 ml of water. An organic layer was separated, dried with 10 g of anhydrous sodium sulfate, and filtered. Subsequently, the product was purified by column chromatograhy using activated alumina, and the solvent was then removed under reduced pressure to give 49 g of a colorless viscous liquid. IR spectrophotometric analysis, NMR analysis and elemental analysis of this product revealed that it was a compound of the following formula [5].

IR spectrophotometric analysis:
1500, 1580, 1610 cm$^{-1}$ (absorption ascribable to an aromatic ring)
1640 cm$^{-1}$ (absorption ascribable to C=C double bond)
1730 cm$^{-1}$ (absorption ascribable to a carbonyl group of a carboxylic acid)

NMR analysis:
1. 9 ppm, singlet corresponding to 6 protons (absorption ascribable to methyl of methacryl)
2. 6 ppm, singlet corresponding to 4 protons (absorption ascribable to methylene derived from succinic acid)
3. 4-3. 9 ppm, multiplet corresponding to 4 protons (absorption ascribable to methylenes on both sides of methine bound to trimellitic acid ester)
4. 1-4. 3 ppm, multiplet corresponding to 1 proton (absorption ascribable to methine bound to trimellitic acid ester)
4. 3 ppm, singlet corresponding to 4 protons (absorption ascribable to methylene derived from hydroxyethyl methacrylate)
5. 6, 6. 2 ppm, doublet corresponding to 4 protons (absorption ascribable to methylene of methacryl)
7. 8-8. 5 ppm, quintet corresponding to 3 protons (absorption ascribable to a benzene ring)
10. 3 ppm, singlet corresponding to 2 protons (absorption ascribable to carboxylic acid)
Elemental analysis (%):
found: 52.29, 5.33,
calculated: 52.28, 5.34,

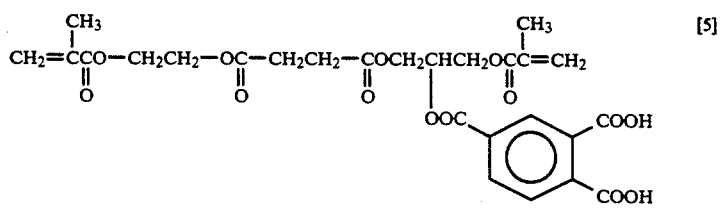

PRODUCTION EXAMPLE 2

A 500 ml three-necked flask was charged with 200 ml of tetrahydrofuran, 38 g of hydroxyproypl acrylate (made by Kyoeisha Yushi Kagaku Kogyo K. K.), 34 g of succinic anhydride (made by Wako Junyaku K. K.) 30 g of pyridine (made by Wako Junyaku K. K.) and a small amount of hydroquinone monoethyl ether (made by Wako Junyaku K. K.). With stirring at 55° to 60° C., the reaction was run for 24 hours. After the reaction was over, the solvent was removed under reduced pressure, and the remaining reaction product was dissolved in 300 ml of benzene. A 5% hydrochloric acid solution was added to the solution until pH became 3 to 4. Then, the separated organic layer was washed with dilute hydrochloric acid and distilled water, and extracted with a dilute sodium carbonate solution. Thereafter, the extract was washed with ether, and a 5% hydrochloric acid solution was added until pH became 3 to 4, followed by extracting the reaction product with ethyl acetate. The extract was dried with anhydrous sodium carbonate, and the solvent was then removed under reduced pressure to obtain 65 g of a colorless liquid.

A 300 ml eggplant type flask was charged with 57 g of the colorless liquid, 28 g of glycidyl methacrylate (made by Wako Junyaku K. K.), 11.4 g of p-toluenesulfonic acid and 100 ml of chloroform, and they were stirred at room temperature for 2 hours. To the reaction liquid was added 200 ml of chloroform, and the mixture was washed with 300 ml of water, 300 ml of a 1N sodium carbonate aqueous solution and 300 ml of water again in this sequence. The organic layer was dried with the addition of 10 g of anhydrous sodium sulfate. After filtration, the solvent was removed under reduced pressure to obtain 59 g of a colorless liquid.

A 500 ml eggplant type flask was charged with 32 g of anhydrotrimellitic acid chloride, 13 g of pyridine and 200 ml of benzene. With stirring under ice cooling, a solution of 57 g of the colorless liquid in 100 ml of benzene was added dropwise over a period of 1 hour, and the reaction solution was then returned to room temperature, followed by stirring said solution for 1 hour. The solution was filtered to remove pyridine hydrochloride, and the solvent was removed from the filtrate under reduced pressure. To the resulting product were added 250 ml of tetrahydrofuran and 250 ml of water, and they were stirred overnight. Three-hundred milliliters of chloroform were added to the solution to extract the product which was then washed twice with 400 ml of water. The organic layer was separated, then dried with the addition of 10 g of anhydrous sodium sulfate, and filtered. The product was purified by column chromatography using activated alumina, and the solvent was then removed under reduced pressure to obtain 40 g of a viscous liquid. IR spectrophotometric analysis, NMR analysis and elemental analysis of this product revealed that it was a compound of the following formula [6]. IR spectrophotometric analysis:

1500, 1580, 1610 cm$^{-1}$ (absorption ascribable to an aromatic ring)

1640 cm$^{-1}$ (absorption ascribable to C=C double bond)

1730 cm$^{-1}$ (absorption ascribable to a carbonyl group of carboxylic acid)

NMR analysis:
1. 9 ppm, singlet corresponding to 3 protons (absorption ascribable to methyl of methacryl) 0.9, 1.0 ppm doublet corresponding to 3 protons (absorption ascribable to methyl of buthyl)
2. 6 ppm, singlet corresponding to 4 protons (absorption ascribable to methylene of succinic acid)
3. 4-3. 9 ppm, multiplet corresponding to 4 protons (absorption ascribable to methylenes on both sides of methine bound to trimellitic acid ester)
4. 1-4. 3 ppm, multiplet corresponding to 3 protons (absorption ascribable to methine bound to trimellitic acid ester and methylene of butyl)
4. 7-5. 2 ppm, multiplet corresponding to 1 proton (absorption ascribable to methine of butyl)
5. 6-6. 4 ppm, multiplet corresponding to 5 protons (absorption ascribable to methylene of methacryl, and methylene and methine of acryl)
7. 8-8. 5 ppm, quintet corresponding to 3 proton (absorption ascribable to a benzene ring)
10. 3 ppm, singlet corresponding to 2 protons (absorption ascribable to carboxylic acid)

|  | Elemental analysis (%) | |
|---|---|---|
|  | C | H |
| Found: | 52.30 | 5.32 |
| calculated: | 52.28 | 5.34 |

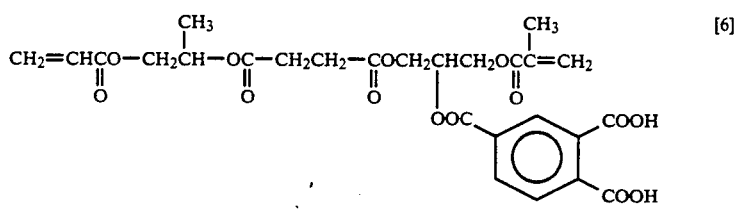

[6]

PRODUCTION EXAMPLE 3

A 500 ml three-necked flask was charged with 200 ml of tetrahydrofuran, 39 g of hydroxyethyl methacrylate (made by Kyoeisha Yushi Kagaku Kogyo K. K.), 29 g of glutaric anhydride (made by Wako Junyaku K. K.), 30 g of pyridine (made by Wako Junyaku K. K.) and a small amount of hydroquinone monomethyl ether (made by Wako Junyaku K. K.). With stirring at 55° to 60° C., the reaction was run for 24 hours. After the reaction was over, the solvent was removed under reduced pressure, and the remaining reaction product was dissolved in 300 ml of benzene. To the solution was added a 5% hydrochloric acid solution until pH became 3 to 4. Then, the separated organic layer was washed with dilute hydrochloric acid and distilled water, and extracted with a dilute sodium carbonate solution. Subsequently, the extract was washed with ether, and a 5% hydrochloric acid solution was added until pH became 3 to 4, followed by extracting the reaction product with ethyl acetate. The extract was dried with anhydrous sodium carbonate, and the solvent was removed under reduced ressure to obtain 66 g of a colorless liquid.

A 300 ml eggplant type flask was charged with 61 g of the colorless liquid, 28 g of glydicyl methacrylate (made by Wako Junyaku K. K.), 11.4 g of p-toluenesulfonic acid and 100 ml of chloroform, and they were stirred at room temperature for 2 hours. To the reaction solution was added 200 ml of chloroform, and the mixture was then washed with 300 ml of water, 300 ml of a 1N sodium carbonate aqueous solution and 300 ml of water again in this sequence. The organic layer was dried with the addition of 10 g of anhydrous sodium sulfate, and filtered, followed by removing the solvent under reduced pressure. There resulted 81 g of the colorless liquid.

A 500 ml eggplant type flask was charged with 32 g of anhydrotrimellitic acid chloride, 13 g of pyridine and 300 ml of benzene. While stirring under ice cooling, 57 g of the colorless liquid was added dropwise over a period of 1 hour, and the reaction liquid was then returned to room temperature and stirred for 1 hour. The solution was filtered, and pyridine hydrochloride was removed The solvent was removed from the filtrate under reduced pressure. To the resulting product were added 250 ml of tetrahydrofuran and 250 ml of water, and they were stirred overnight. Three-hundred milliliters of chloroform were added to the solution to extract the product which was then washed twice with 400 ml of water. The organic layer was separated, dried with the addition of 10 g of anhydrous sodium sulfate, and filtered. The product was formed by column chromatography using activated alumina. The solvent was then removed under reduced pressure to obtain 40 g of a viscous liquid. IR spectrophotometric analysis, NMR analysis and elemental analysis of this product revealed that it was a compound of the following formula [7].

IR spectrophotometric analysis:
1500, 1580, 1610 cm$^{-1}$ (absorption ascribable to an aromatic ring)
1640 cm$^{-1}$ (absorption ascribable to C=C double bond)
1730 cm$^{-1}$ (absorption ascribable to a carbonyl group of carboxylic acid)

NMR analysis:
1. 9 ppm, singlet corresponding to 6 protons (absorption ascribable to methyl of methacryl)
1. 3-1. 8 ppm, multiplet corresponding to 2 protons (absorption ascribable to methylene in the center of glutaric acid)
2 2-2. 4 ppm, quartet corresponding to 4 protons (absorption ascribable to methylenes on the right and left of glutaric acid)
3. 4-3. 9 ppm, multiplet corresponding to 4 protons (absorption ascribable to methylenes on both sides of methine of trimellitic acid ester)
4. 1-4. 3 ppm, multiplet corresponding to 1 proton (absorption ascribable to methine bound to trimellitic acid ester)
4. 3 ppm, singlet corresponding to 4 protons (absorption ascribable to methylene of hydroxyethyl methacrylate)
5. 6, 6. 2 ppm, doublet corresponding to 4 protons (absorption ascribable to methylene of methacryl)
7. 8-8. 5 ppm, quintet corresponding to 3 protons (absorption ascribable to a benzene ring)
1 10. 3 ppm, singlet corresponding to 2 protons (absorption ascribable to carboxylic acid)

|  | Elemental analysis (%) | |
|---|---|---|
|  | C | H |
| found: | 52.30 | 5.32 |
| calculated: | 52.28 | 5.34 |

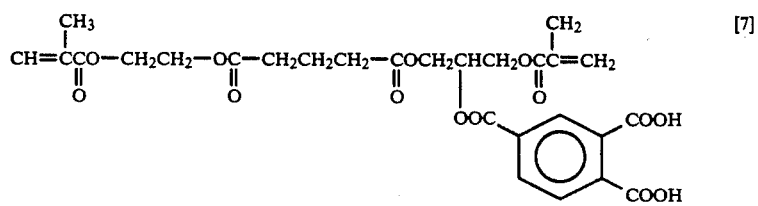

[7]

PRODUCTION EXAMPLE 4

A 200 ml eggplant type flask was charged with 16.8 g of trimellitic acid chloride, 6.3 g of pyridine and 80 ml of benzene. While stirring under ice cooling, a benzene solution of 28.4 g of pentaerythritol triacrylate (made by Osaka Yuki Kagaku Kogyo K. K.) was added dropwise over a period of 30 minutes. After the dropwise addition, the solution was stirred at room temperature for 1 hour, and the resulting reaction liquid was washed thrice with deionized water. To the solution were added 80 ml of tetrahydrofuran and 100 ml of deionized water, and the solution was vigorously stirred overnight at room temperature. The reaction mixture was then dried with sodium sulfate. The resulting product was purified by silica gel column chromatography to obtain 21.2 g of a white waxy solid. IR spectrophotometric analysis, NMR analysis and elemental analysis of this product revealed that it was a compound of the following formula [8].

|  | Elemental analysis (%): | |
|---|---|---|
|  | C | H |
| found: | 81.54 | 6.58 |
| calculated: | 81.55 | 6.56 |

IR spectrophotometric analysis:
1500, 1580, 1610 cm$^{-1}$ (absorption ascribable to anaromatic ring)
1640 cm$^{-1}$ (absorption ascribable to C=C double bond)
1730 cm$^{-1}$ (absorption ascribable to a carbonyl group of carboxylic acid)

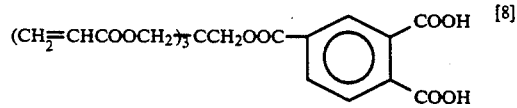

[8]

EXAMPLE 1

A mixed powder obtained by mixing 120 g of silica, 42 g of aluminum hydroxide, 28 g of artificial cryolite, 78 g of aluminum phosphate, 24 g of aluminum fluoride and 76 g of calcium fluoride with a ball mill for 3 hours was charged in a platinum crucible, and heat-melted at 1,400° C. for 30 seconds. Subsequently, the melt was quenched in a water bath, and the resulting glass was pulverized in a vibration ball mill. The thus obtained powder was put through a 400-mesh nylon sieve, and 500 g of the powder passing though the sieve was dispersed in 1 liter of methanol. The powder (hereinafter referred to as a "filler A") precipitated within 1 hour was collected. The filler A had a particle size of 0.2 to 2.7 micrometers, an average particle size of 1.0 micrometer, and a polyvalent metallic ion dissolving amount of 16 mgeq/g. Said filler was amorphous.

Ten grams of a mixture obtained by dissolving 0.5 part by weight of camphorquinone and 0.5 part by weight of p-dimethylaminobenzoic acid ethyl ester in a monomer mixture of 80 parts by weight of an acid group-containing vinyl monomer of formula [5] formed according to Production Example 1 were mixed with 15 g of the filler A by shielding light, and then defoamed in vacuo to prepare a curable composition.

The curable composition had adhesion strength to dentin of 85 kg/cm$^2$ and 83 kg/cm$^2$ under humidity, tensile strength of 312 kg/cm$^2$, compressive strength of 2,670 kg/cm$^2$, and an amount of coffee coloration of $\Delta E^* = 8.4$.

EXAMPLE 2

Ten grams of a mixture obtained by dissolving 1.0 part by weight of camphorquinone and 1.0 part by weight of p-dimethylaminobenzoic acid ethyl ester in a monomer mixture of 50 parts by weight of the acid group-containing vinyl monomer of formula [6] obtained according to said Production Example 2 and 50 parts by weight of hydroxyethyl methacrylate were mixed with 15 g of the filler A by shielding light, and the mixture was defoamed in vacuo to prepare a curable composition.

The curable composition had adhesion strength to dentin of 73 kg/cm$^2$ and 69 kg/cm$^2$ under humidity, tensile strength of 331 kg/cm$^2$, compressive strength of 2,910 kg/cm$^2$, and an amount of coffee coloration of $\Delta E^* = 9.1$.

EXAMPLE 3

Ten grams of a mixture obtained by dissolving 0.5 part by weight of camphorquinone and 0.5 part by weight of p-dimethylaminobenzoic acid ethyl ester in a monomer mixture of 80 parts by weight of the acid group-containing vinyl monomer of formula [7] formed according to said Production Example 3 and 20 parts by weight of triethylene glycol dimethacrylate were mixed with 15 g of the filler A by shielding light, and the mixture was defoamed in vacuo to produce a curable composition.

The curable composition had adhesion strength to dentin of 71 kg/cm$^2$ and 74 kg/cm$^2$ under humidity, tensile strength of 348 kg/cm$^2$, compressive strength of 3,230 kg/cm$^2$, and an amount of coffee coloration of $\Delta E^* = 6.5$.

EXAMPLES 4 to 6

A test was run as in Example 1 except that a fluoroaluminosilicate glass shown in Table 1 was produced and used as an ion leachable filler.

The results in Examples 1 and 4 to 6 are shown in Table 1.

COMPARATIVE EXAMPLES 1 AND 2

Using a commercial dental composite resin (Palfique Light: a trademark for a product of Tokuyama Soda Co., Ltd. comprising, as main components, an acid group-free multifunctional vinyl monomer, a silica filler and an alpha-diketone polymerization initiator) and a bonding agent [Comparative Example 1] as well as a glass ionomer cement for dental filling (FUJI IONOMER II: a trademark for a product of G-C Dental Industrial Corp. comprising, as main components, a polycarboxylic acid aqueous solution and a fluoroaminosilicate glass)-[Comparative Example 2], the test was carried out. The test results are shown in Table 1.

TABLE 1

| | Glass composition | | | | | | Polyvalent ion dissolving amount of a filler (mgeq/g) | Adhesion to dentin: The parenthesized are values under humidity (kg/cm$^2$) | Tensile strength (kg/cm$^2$) | Compressive strength (kg/cm$^2$) | Amount of coffee coloration ($\Delta E^*$) |
|---|---|---|---|---|---|---|---|---|---|---|---|
| | Silica (g) | Aluminum hydroxide (g) | Artificial cryolite (g) | Aluminum phosphate (g) | Aluminum fluoride (g) | Calcium fluoride (g) | | | | | |
| Example 1 | 120 | 42 | 28 | 78 | 24 | 76 | 16 | 85(83) | 312 | 2670 | 8.4 |
| Example 4 | 120 | 37 | 28 | 86 | 24 | 68 | 14 | 82(85) | 308 | 2910 | 8.7 |
| Example 5 | 120 | 32 | 28 | 94 | 24 | 61 | 13 | 75(72) | 322 | 3010 | 8.2 |
| Example 6 | 120 | 27 | 28 | 101 | 24 | 53 | 11 | 70(74) | 303 | 2890 | 9.3 |
| Comparative Example 1 | — | — | — | — | — | — | — | 29(16) | 431 | 3630 | 7.2 |
| Comparative Example 2 | — | — | — | — | — | — | — | 34(31) | 72 | 1820 | 5.9 |

Ten grams of a mixture obtained by dissolving 0.5 part by weight of camphorquinone and 0.5 part by weight of p-dimethylaminobenzoic acid ethyl ester in a monomer mixture of 80 parts by weight of the acid group-containing vinyl monomer of formula [5] and 20 parts by weight of neopentylglycol dimethacrylate were mixed with 20 g of the filler A by shielding light, and the mixture was defoamed in vacuo to produce a curable composition.

The curable composition had adhesion strength to dentin of 72 kg/cm$^2$ and 68 kg/cm$^2$ under humidity, tensile strength of 320 kg/cm$^2$, compressive strength of 2,990 kg/cm$^2$ and an amount of coffee coloration of $\Delta E^* = 5.9$.

EXAMPLE 8

Fifteen grams of a mixture obtained by dissolving 0.5 part by weight of camphorquinone and 0.5 part by weight of p-dimethylaminobenzoic acid ethyl ester in a monomer mixture of 60 parts by weight of the acid group-containing vinyl monomer of formula [5], 20 parts by weight of a difunctional vinyl monomer (D-2.6E: a trademark for a product of Shin Nakamura Kagaku K. K., represented by the following formula) and 20 parts by weight of triethylene glycol dimethacrylate (made by Shin Nakamura Kagaku K. K.) were mixed with 12 g of the filler A.

D-2.6E:

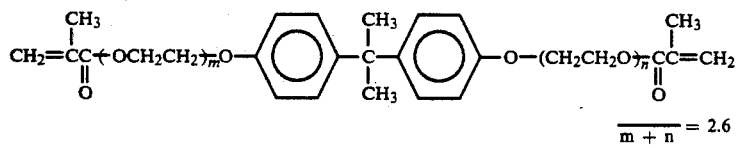

The curable composition had adhesion strength to dentin of 65 kg/cm$^2$ and 69 kg/cm$^2$ under humidity, tensile strength of 292 kg/cm$^2$, compressive strength of 2,730 kg/cm$^2$, and an amount of coffee coloration of $\Delta E^* = 5.2$.

EXAMPLE 9

Eighty grams of the acid group-containing vinyl monomer of formula [5] were mixed with 20 parts by weight of hydroxyethyl methacryate to prepare a monomer solution. Ten grams of a mixture obtained by dissolving 1.0 part by weight of N,N'-di(beta-hydroxyethyl)-p-toluidine in the monomer solution were mixed with 15 g of the filler A to form a paste I. Then, 10 g of a mixture obtained by dissolving 1.2% by weight of benzoyl peroxide in the monomer solution was mixed with 15 g of the filler to form a paste II. The pastes I and II were mixed at a weight ratio of 1:1, and the product was tested. Said product had adhesion strength to dentin of 71 kg/cm$^2$ and 68 kg/cm$^2$ under humidity, tensile strength of 283 kg/cm$^2$, compressive strength of 2,640 kg/cm$^2$, and an amount of coffee coloration of $\Delta E^* = 9.2$.

EXAMPLE 10

During the production of the filler in Example 1, the powder precipitated in methanol within 1 hour was collected, and fed into a burning chamber from a burner having a multiple tube at a feed rate of 20 g/min together with hydrogen (2.3 Nm$^3$/hr) and oxygen (0.90 Nm$^3$/hr), dispersed in flame and melted. After the particles were instantaneously melted in flame and then came out from the flame, said particles were cooled, solidified and recovered with a cyclon. Further, 10 g of the powder was kneaded with 0.4 g of ammonium fluoride and a small amount of water. The mixture was then dried at 100° C. for 3 hours, and heated at 600° C. for 1 hour. The thus obtained powder (referred to as a "filler B") was 100 % spherical. The powder had a particle size of 3.7 to 18.1 micrometers, an average particle size of 7.8 micrometers and a polyvalent metallic ion dissolving amount of 11 meq/g. Said powder was amorphous.

Eight grams of a mixture obtained by dissolving 0.5 part by weight of camphorquinone and 0.5 part by weight of p-dimethylaminobenzoic acud ethyl ester in a monomer mixture of 50 parts by weight of the acid group-containing vinyl monomer of formula [5] and 50 parts by weight of hydroxyethyl methacrylate were mixed with 11 g of the filler A and 17 g of the filler B by shielding light, and the mixture was defoamed to prepare a curable composition.

The curable composition had adhesion strength to dentin of 69 kg/cm$^2$ and 72 kg/cm$^2$ under humidity, tensile strength of 309 kg/cm$^2$, compressive strength of 3,360 kg/cm$^2$, and an amount of coffer coloration of $\Delta E^* = 8.8$.

COMPARATIVE EXAMPLE 3

Ten grams of a mixture obtained by dissolving 0.5 part by weight of camphorquinone and 0.5 part by weight of p-dimethylaminobenzoic acid ethyl ester in 100 parts by weight of an acid group-containing vinyl monomer (M-5500: a trademark for a product of Toagosei Chemical Industry Co., Ltd., represented by the following formula) were mixed with 20 g of the filler A by shielding light, and the mixture was defoamed in vacuo to prepare a curable composition.

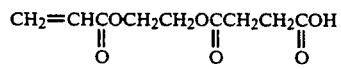

The curable composition had adhesion strength to dentin of 83 kg/cm$^2$ and 77 kg/cm$^2$ under humidity, tensile strength of 213 kg/cm$^2$, compressive strength of 1,220 kg/cm$^2$, and an amount of coffee coloration of $\Delta E^* = 25.1$.

COMPARATIVE EXAMPLE 4

Ten grams of a mixture obtained by dissolving 0.5 part by weight of camphorquinone and 0.5 part by weight of p-dimethylaminobenzoic acid ethyl ester in 100 parts by weight of a monomer mixture of 48 parts by weight of a difunctional vinyl monomer (D-GMA: a trademark for a product of Shin Nakamura Kagaku K. K., represented by the following formula), 24 parts by weight of a difunctional vinyl monomer (D-2.6E), 4 parts by weight of an acid group-containing vinyl monomer represented by the following formula and 24 parts by weight of a difunctional vinyl monomer (ART RESIN SH-400: a trademark for a product of Shin Nakamura Kagaku K. K., having a urethane linkage, as represented by the following formula) were mixed with 20 g of the filler A by shielding light, and defoamed in vacuo to prepare a curable composition.

D-GMA:

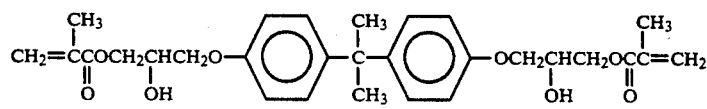

Acid group-containing vinyl monomer

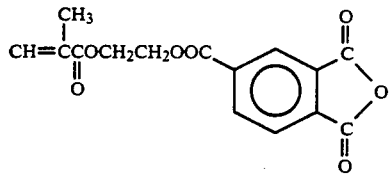

ART RESIN SH 400:

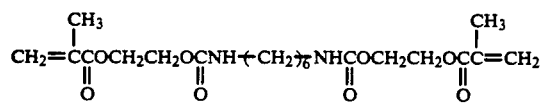

The curable composition had adhesive strength to dentin of 19 kg/cm² and 10 kg/cm² under humidity, tensile strength of 342 kg/cm², compressive strength of 3,580 kg/cm², and an amount of coffee coloration of $\Delta E^* = 5.8$.

COMPARATIVE EXAMPLE 5

Ten grams of a mixture obtained by dissolving 0.5 part by weight of camphorquinone and 0.5 part by weight of p-dimethylaminobenzoic acid ethyl ester in 100 parts by weight of a monomer mixture of 48 parts by weight of a difunctional vinyl monomer (D-GMA), 24 parts by weight of a difunctional vinyl monomer (D-2.6E), 4 parts by weight of the same acid-group containing vinyl monomer as used in Comparative Example 4 and 24 parts by weight of a difunctional vinyl monomer (ART RESIN SH-400) were mixed with 10 g of a titanium oxide powder by shielding light, and defoamed in vacuo to prepare a curable composition.

The curable composition had adhesive strength to dentin of 11 kg/cm² and 9 kg/cm² under humidity, tensile strength of 321 kg/cm², compressive strength of 3,160 kg/cm², and an amount of coffee coloration of $\Delta E^* = 14.8$.

COMPARATIVE EXAMPLE 6

Ten grams of a mixture obtained by dissolving 0.5 part by weight of camphorquinone and 0.5 part by weight of p-dimethylaminobenzoic acid ethyl ester in 100 parts by weight of a monomer mixture of 20 parts by weight of the acid group-containing vinyl monomer of formula [5] and 80 parts by weight of neopentyl glycol dimethacrylate were mixed with 15 g of the filler A by shielding light, and defoamed in vacuo to prepare a curable composition.

The curable composition had adhesive strength to dentin of 23 kg/cm² and 18 kg/cm² under humidity, tensile strength of 263 kg/cm², compressive strength of 2,570 kg/cm², and an amount of coffee coloration of $\Delta E^* = 5.9$.

COMPARATIVE EXAMPLE 7

Ten grams of a mixture obtained by dissolving 0.5 part by weight of camphorquinone and 0.5 part by weight of p-dimethylaminobenzoic acid ethyl ester in a monomer mixture of 80 parts by weight of the acid group-containing vinyl monomer of formula [5] and 20 parts by weight of hydroxyethyl methacrylate were mixed with 15 g of cristobalite by shielding light, and defoamed in vacuo to prepare a curable composition.

The curable composition had adhesive strength to dentin of 50 kg/cm² and 62 kg/cm² under humidity, tensile strength of 231 kg/cm², compressive strength of 1,920 kg/cm², and an amount of coffee coloration $\Delta E^* = 13.1$.

COMPARATIVE EXAMPLE 8

Ten grams of a mixture obtained by dissolving 0.5 part by weight of camphorquinone and 0.5 part by weight of p-dimethylaminobenzoic acid ethyl ester in a monomer mixture of 80 parts by weight of the acid group-containing vinyl monomer of formula [5]and 20 parts by weight of hydroxyethyl methacrylate were mixed with 2 g of the filler A by shielding light, and defoamed in vacuo to prepare a curable composition.

The curable composition had adhesive strength to dentin of 41 kg/cm² and 35 kg/cm² under humidity, tensile strength of 223 kg/cm², compressive strength of 1,940 kg/cm², and an amount of coloration of $\Delta E^* = 10.6$.

EXAMPLE 11

Ten grams of a mixture obtained by dissolving 0.5 part by weight of camphorquinone and 0.5 part of p-dimethylaminobenzoic acid ester in a monomer mixture of 80 parts by weight of the acid group-containing vinyl monomer of formula [8] and 20 parts by weight of hydroxyethyl methacrylate were mixed with 20 g of the filler A by shielding light, and defoamed in vacuo to prepare a curable composition.

The curable composition had adhesive strength to dentin of 87 kg/cm² and 81 kg/cm² under humidity, tensile strength of 289 kg/cm², and an amount of coffee coloration of $\Delta E^* = 6.9$.

EXAMPLES 12 to 14

The test was performed as in Example 11 except using a fluoroaluminosilicate glass of a composition different from that in Example 11, as shown in Table 2. The results are shown in Table 2.

TABLE 2

| | Glass composition | | | | | | Polyvalent ion dissolving amount of a filler (mgeq/g) | Adhesion to dentin: The parenthesized are values under humidity (kg/cm²) | Tensile strength (kg/cm²) | Amount of coffee coloration ($\Delta E^*$) |
|---|---|---|---|---|---|---|---|---|---|---|
| | Silica (g) | Aluminum hydroxide (g) | Artificial cryolite (g) | Aluminum phosphate (g) | Aluminum fluoride (g) | Calcium fluoride (g) | | | | |
| Example 11 | 120 | 42 | 28 | 78 | 24 | 76 | 16 | 87(81) | 289 | 6.9 |
| Example 12 | 120 | 37 | 28 | 86 | 24 | 68 | 14 | 81(83) | 277 | 7.3 |
| Example 13 | 120 | 32 | 28 | 94 | 24 | 61 | 13 | 75(80) | 264 | 7.9 |
| Example 14 | 120 | 27 | 28 | 101 | 24 | 53 | 11 | 79(76) | 273 | 7.1 |
| Comparative Example 1 | — | — | — | — | — | — | — | 29(16) | 431 | 7.2 |
| Comparative Example 2 | — | — | — | — | — | — | — | 34(31) | 72 | 5.9 |

EXAMPLE 15

Ten grams of a mixture obtained by dissolving 0.5 part by weight of camphorquinone and 0.5 part by weight of p-dimethylaminobenzoic acid ethyl ester in a monomer mixture of 50 parts by weight of an acid group-containing vinyl monomer represented by the following formula and 50 parts by weight of a difunctional vinyl monomer (D-2.6E) were mixed with 20 g of the filler A by shielding light, and defoamed in vacuo to prepare a curable composition.

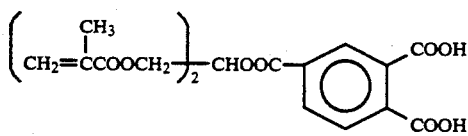

The curable composition had adhesive strength to dentin of 80 kg/cm$^2$ and 76 kg/cm$^2$ under humidity, tensile strength of 272 kg/cm$^2$, and an amount of coffee coloration of $\Delta E^* = 8.1$.

EXAMPLE 16

Ten grams of a mixture obtained by dissolving 0.5 part by weight of camphorquinone and 0.5 part by weight of p-dimethylaminobenzoic acid ethyl ester in a monomer mixture of 90 parts by weight of an acid group-containing vinyl monomer represented by the following formula and 10 parts by weight of a difunctional vinyl monomer (NPG: a trademark for a product of Shin Nakamura Kagaku K. K.) were mixed with 30 g of the filler A by shielding light, and defoamed in vacuo to prepare a curable composition.

Acid group-containing vinyl monomer:

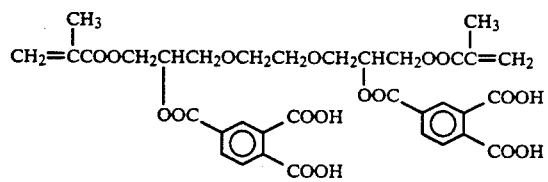

NPG:

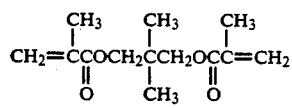

The curable composition had adhesive strength to dentin of 74 kg/cm$^2$ and 79 kg/m$^2$ under humidity, tensile strength of 249 kg/cm$^2$, and an amount of coffee coloration of $\Delta E^* = 9.4$.

EXAMPLE 17

Ten grams of a mixture obtained by dissolving 1.0 part by weight of N,N'-di(beta-hydroxyethyl)-p-toluidine in a monomer solution of 80 parts by weight of the acid group-containing vinyl monomer of formula [8] and 20 parts by weight of triethylene glycol dimethacrylate (made by Shin Nakamura Kagaku K. K.) were mixed with 20 g of the filler A to form a paste I. Then, 10 g of a mixture obtained by dissolving 1.2 parts by weight of benzoyl peroxide in 100 parts by weight of the monomer solution was mixed with 10 g of the filler A to form a paste II. The pastes I and II were mixed at a weight ratio of 1:1, and the product was tested. As a result, said product had adhesive strength to dentin of 68 kg/cm$^2$ and 73 kg/cm$^2$ under humidity, tensile strength of 267 kg/cm$^2$, and an amount of coffee coloration $\Delta E^* = 8.6$.

EXAMPLE 18

Ten grams of a mixture obtained by dissolving 0.5 part by weight of camphorquinone and 0.5 part by weight of p-dimethylaminobenzoic acid ethyl ester in a monomer mixture of 60 parts by weight of the acid group-containing vinyl monomer of formula [8] and 40 parts by weight of triethylene glycol were mixed with 24 g of the filler A and 16 g of the filler B by shielding light, and defoamed in vacuo to prepare a curable composition.

The curable composition had adhesive strength to dentin of 71 kg/cm$^2$ and 67 kg/cm$^2$ under humidity, tensile strength of 297 kg/cm$^2$, and an amount of coffee coloration of $\Delta E^* = 6.1$.

COMPARATIVE EXAMPLE 9

Ten grams of a mixture obtained by dissolving 0.5 part by weight of camphorquinone and 0.5 part by weight of p-dimethylaminobenzoic acid ethyl ester in 100 parts by weight of an acid group-containing vinyl monomer (M-5500) were mixed with 20 g of the filler A by shielding light, and defoamed in vacuo to prepare a curable composition.

The curable composition had adhesive strength to dentin of 83 kg/cm$^2$ and 77 kg/cm$^2$ under humidity, tensile strength of 213 kg/cm$^2$, and an amount of coffee coloration of $\Delta E^* = 25.1$.

COMPARATIVE EXAMPLE 10

Ten grams of a mixture obtained by dissolving 0.5 part by weight of camphorquinone and 0.5 part by weight of p-dimethylaminobenzoic acid ethyl ester in a monomer mixture of 80 parts by weight of an acid group-containing vinyl monomer represented by the following formula and 20 parts by weight of hydroxymethacrylate were mixed with 20 g of the filler A by shielding light, and defoamed in vacuo to prepare a curable composition.

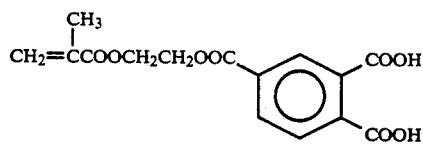

The resin composition had adhesive strength to dentin of 42 kg/cm$^2$ and 37 kg/cm$^2$ under humidity, tensile strength of 99 kg/cm$^2$, and an amount of coffee coloration of $\Delta E^* = 15.5$.

COMPARATIVE EXAMPLE 11

Ten grams of a mixture obtained by dissolving 0.5 part by weight of camphorquinone and 0.5 part by weight of p-dimethylaminobenzoic acid ethyl ester were mixed with 22 g of the filler A by shielding light, and then defoamed in vacuo to prepare a curable composition.

The curable composition had adhesive strength to dentin of 23 kg/m$^2$ and 11 kg/m$^2$ under humidity, tensile strength of 308 kg/cm$^2$, and an amount of coffee coloration of $\Delta E^* = 6.5$.

COMPARATIVE EXAMPLE 12

Ten grams of a mixture obtained by dissolving 0.5 part by weight of camphorquinone and 0.5 part by weight of p-dimethylaminobenzoic acid ethyl ester to a mixture of 80 parts by weight of the acid group-containing vinyl monomer of formula (8) and 20 parts by weight of hydroxyethyl methacrylate were mixed with 20 g of a powder formed by surface-treating pulverized quartz (VXS: a trademark for a product of Tatsumori Ltd.) with gamma-methacryloxypropyltrimethoxysilane by shielding light, and defoamed in vacuo to prepare a curable composition.

The curable composition had adhesive strength to dentin of 48 kg/cm$^2$ and 65 kg/cm$^3$ under humidity, tensile strength of 295 kg/cm$^2$, and an amount of coffee coloration of $\Delta E^* = 14.8$.

EFFECTS OF THE INVENTION

Since the curable composition of this invention shows high adhesion even in the presence of water, development of adhesive strength can surely be expected in clinical treatment such as restoration of teeth.

Further, when the cured product is used as a dental filling material, no decrease in adhesive strength due to its destruction is found because of higher tensile strength than that of the glass ionomer cement, as well as wear and breakage little occur. Besides, it does not require a bonding agent indispensable in the composite resin to make a clinical system simple.

Still further, there is little coloration owing to food and beverage in a mouth.

Because of the foregoing characteristics, the curable composition of this invention can be used as a dental filling material, a bonding agent of a composite resin, a backing material, a dental sealant, and other filling materials and bonding agents.

What we claim is:

1. A curable composition for dental restoration comprising (A) 100 parts by weight of a vinyl monomer containing not less than 30 % by weight of an acid group-containing vinyl monomer represented by formula [1]

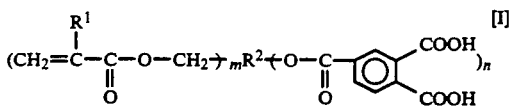

wherein R$^1$'s may be the same or different and each denotes a hydrogen atom or a methyl group, R$^2$ denotes a trivalent to hexavalent organic residue having 1 to 30 carbon atoms which residue may have an ether linkage and/or an ester linkate, m is an integer of 2 to 4, and n is an integer of 1 or 2, (B) 30 to 500 parts by weight of an ion leachable filler that dissolves 2 mgeq/g to 60 mgeq/g of a polyvalent metallic ion, and (C) 0.1 to 3 parts by weight of a polymerization initiator.

2. The curable composition of claim 1 wherein in formula R$^2$ is a trivalent or tetravalent hydrocarbon group having 1 to 20 carbon atoms which group may have an ether linkage or an ester linkage, m is an integer of 2 or 3.

3. The curable composition of claim 2 wherein the acid group-containing vinyl monomer is an acid group-containing vinyl monomer represented by the formula

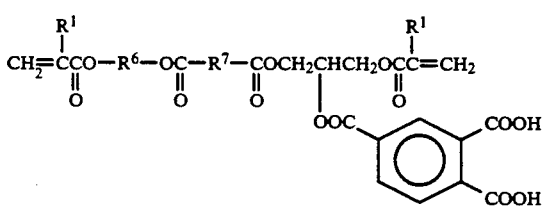

wherein R$^1$'s may be the same or different and each denotes a hydrogen atom or a methyl group, and R$^6$ and R$^7$ are alkylene groups having 1 to 4 carbon atoms.

* * * * *